United States Patent
Thompson et al.

(10) Patent No.: US 6,177,430 B1
(45) Date of Patent: Jan. 23, 2001

(54) USE OF $\alpha_1$-ADRENORECEPTOR ANTAGONISTS IN THE PREVENTION AND TREATMENT OF BENIGN PROSTATIC HYPERPLASIA

(75) Inventors: Timothy C Thompson; Guang Yang, both of Houston, TX (US); Michael G Wyllie, New York, NY (US)

(73) Assignee: Pfizer Inc, New York, NY (US)

( * ) Notice: Under 35 U.S.C. 154(b), the term of this patent shall be extended for 0 days.

(21) Appl. No.: 09/415,671

(22) Filed: Oct. 12, 1999

Related U.S. Application Data

(63) Continuation of application No. 08/827,124, filed on Mar. 27, 1997, now abandoned.

(51) Int. Cl.$^7$ ...................... A61K 31/496; A61K 31/517
(52) U.S. Cl. .......................................................... 514/252.17
(58) Field of Search ................................ 514/254, 252.17

(56) References Cited

U.S. PATENT DOCUMENTS

| | | | |
|---|---|---|---|
| 4,112,097 | 9/1978 | Winn et al. | 424/251 |
| 4,503,067 | 3/1985 | Wiedemann et al. | 514/411 |
| 4,758,569 | 7/1988 | Swindell | 514/254 |
| 4,868,216 | 9/1989 | Imai et al. | 514/603 |
| 4,987,152 | 1/1991 | Imai et al. | 514/603 |
| 5,415,873 | 5/1995 | Trepel et al. | 424/422 |
| 5,436,264 | 7/1995 | Pfister et al. | 514/415 |
| 5,508,279 | 4/1996 | Gray | 514/254 |
| 5,620,993 | 4/1997 | Patane et al. | 514/321 |
| 5,661,163 | 8/1997 | Patane et al. | 514/331 |
| 5,753,641 | 5/1998 | Gormley et al. | 514/179 |
| 5,780,485 | 7/1998 | Gluchowski et al. | 514/318 |

FOREIGN PATENT DOCUMENTS

| | | |
|---|---|---|
| 0564093 | 2/1993 | (EP) . |
| 0582502 | 7/1993 | (EP) . |
| 0673650 | 3/1995 | (EP) . |
| 9504072 | 2/1995 | (WO) . |
| 9528157 | 10/1995 | (WO) . |
| 9528932 | 11/1995 | (WO) . |
| 9622992 | 8/1996 | (WO) . |

OTHER PUBLICATIONS

Kenny, B. et al., Exp. Opin. Invest. Drugs, 4(10), 915–23, 1995.*

H. Lepor, et al., The safety and efficacy of terazosin for the treatment of benign prostatic hyperplasia; J. of Clinical Pharmacology; (1989); vol. 27, No. 8; pp. 392–397.

Roger S. Kirby; Doxazosin in Benign Prostatic Hyperplasia; Effects on blood Pressure and Urinary Flow in Normotensive and Hyertensive Men; The J. of Urology; (1995); vol. 46, No. 2; pp. 182–186.

Masahiro Aihare, et al.; Frequency of Apoptotic Bodies Positively Correlates with Gleason Grade in Prostate Cancer; Human Pathology; (1994); vol. 25, No. 8; pp. 797–801.

K. Slawin, et al.; Dietary Fenretinide, a Synthetic Retinoid, Decreases the Tumor Incidence and the Tumor Mass of ras+myc–induced Carcinomas in the Mouse Prostate Reconstitution Model System; Cancer Research; (1993); vol. 53; pp. 4461–4465.

Steven A. Kaplan, et al.; Doxazosin in Physiologically and Pharmacologically Normotensive Men with Benign Prostatic Hyperplasia; The J. of Urology; (1995); vol. 46, No. 4; pp. 512–517.

Ahmed Fawzy, et al.; Doxazosin in the treatment of benign prostatic hyperplasia in normotensive patients: A multicenter study; The J. of Urology; (1995); vol. 154; pp. 105–109.

* cited by examiner

*Primary Examiner*—Phyllis G. Spivack
(74) *Attorney, Agent, or Firm*—Peter C. Richardson; Paul H. Ginsburg; Israel Nissenbaum

(57) ABSTRACT

A method for reducing the extent of or preventing further hyperplasia in BPH in a mammal which comprises administering to said mammal an effective amount of a drug comprising an $\alpha_1$-adrenoreceptor antagonist or pharmaceutically acceptable acid addition salt thereof.

10 Claims, No Drawings

USE OF $\alpha_1$-ADRENORECEPTOR ANTAGONISTS IN THE PREVENTION AND TREATMENT OF BENIGN PROSTATIC HYPERPLASIA This application is a continuation of application Ser. No. 08/827,124, filed Mar. 27, 1997, now abandoned.

BACKGROUND OF THE INVENTION

1. Field of the Invention

This invention relates to the use of $\alpha_1$-adrenoreceptor antagonists, or pharmaceutically acceptable acid addition salts, thereof for treating or preventing the formation of benign prostatic hyperplasia (BPH) in mammals. More particularly, it relates to a method for preventing the formation of, or reducing, BPH in mammals by administering to said mammals an $\alpha_1$-adrenoreceptor antagonist or pharmaceutically acceptable acid addition salt thereof.

2. General Background

Benign prostatic hyperplasia (BPH) is one of the most common, nonmalignant neoplastic processes to affect the aging man. Symptoms occur in about 50 and up to 80% of men 60 years old and older than 80 years, respectively. In the United States BPH is an important health problem resulting in an estimated 1.7 million visits to physicians offices each year.

BPH results from a progressive enlargement of the prostate, leading to urethral constriction, a disturbance in normal urinary outfow, urinary retention and associated irritative symptoms. In symptomatic BPH there appear to be two components of the urethral obstruction: a static component related to prostatic mass and a dynamic component related to the noradrenergic tone in the prostatic and urethral smooth muscle. A number of functional studies have shown that the contractile response is primarily mediated by $\alpha_1$-adrenoreceptors. Autoradiographical data suggest that these are primarily located on stromal smooth muscle.

Since approximately 50% of prostatic outflow obstruction in a patient is mediated by the sympathetic nervous system and, therefore, are potentially reversible it would be expected that urinary outflow obstruction and disease related symptoms would be relieved by $\alpha_1$-adrenoreceptor antagonists.

Early studies of phenoxybenzamine (a nonselective $\alpha_1$ and $\alpha_2$ adrenoreceptor antagonist) and prazosin (a selective $\alpha_1$-adrenoreceptor antagonist) were effective in in the treatment of BPH with the selective $\alpha_1$ agent producing fewer and more tolerable side effects than the nonselective phenoxybenzamine. In a meta-analysis of literature data the $\alpha_1$-adrenoreceptor antagonists produced a 51% decrease in BPH symptom scores, improved urinary flow rate and post-void residual volume without increasing the risk of incontinence, impotence or other adverse effects associated with surgery for BPH.

Kenny, B. et al. ($\alpha_1$-Adrenoreceptor Antagonists As Treatments For Benign Prostatic Hyperplasia, *Exp. Opin. Invest. Drugs*, (1995), 4(10), 915–23), incorporated herein in its entirety by reference) have discussed the use of a number of $\alpha_1$-adrenoreceptor antagonists, such as terazosin, doxazosin and its 6'- and 7'-hydroxy metabolites, indoramin and tamsulosin forthe treatment of symptoms of BPH. However, they did not suggest that $\alpha_1$-adrenoreceptor antagonists could be used to prevent the formation of BPH or, if formed, treatment thereof to decrease the tumors.

Kaplan, S. A. et al, (*Urology*, 46(4), 1995, 512–17), Kirby, R. S. (*Urology*, 46(2), 1995, 182–6) and Fawzy, A. et al. (The Journal of Urology, 154 105–9 (1995)) have discussed the effect of doxasocin on the blood pressure of normotensive men who are being treated with doxazosin for mediation of the dynamic component of smooth muscle prostate outflow obstruction. However, they have not suggested that $\alpha_1$-adrenoreceptor antagonists could be used to prevent the formation of BPH or, if formed, treatment thereof to decrease the tumors.

Doxazosin, 4-amino-2-[4-(1-4-benzodioxan-2-carbonyl)piperazin-1-yl]-6,7-dimethoxyquinazoline and its pharmaceutically acceptable acid addition salts, are described in U.S. Pat. No. 4,188,390 together with their use as regulators of the cardiovascular system, especially in the treatment of hypertension.

U.S. Pat. No. 4,758,569 claims the use of doxazosin in retarding development of atherosclerosis in a mammal. The use of trimazosin or a pharmaceutically acceptable acid salt thereof, for retarding atherosclerosis is described and claimed in U.S. Pat. No. 4,582,832.

U.S. Pat. Nos. 4,868,216 and 4,987,152 claim the use of tamsulosin and its hydrochloride for producing $\alpha_1$-adrenoreceptor antagonistic action, or treating urinary tract dysfunction, respectively, in a host.

$\alpha_1$-Adrenoreceptor antagonists such as 2,4,6,7-tetrasubstituted quinazolines are disclosed in U.S. Pat. Nos. 3,511,836, 4,001,237 and 4,188,390 for use as hypertensive agents. U.S. Pat. No. 4,112,097 also claims the use of terazosin, and its tetrahydropyran-2-carbonyl homologue, for treatment of hypertension in mammals. The references do not disclose the use of those compounds for preventing the formation of, or reducing, BPH in a mammal.

Despite the many patents and studies, such as those above, relating to the use of $\alpha_1$-adrenoreceptor antagonists in the treatment of hypertension, atherosclerosis, urinary tract dysfunction and smooth muscle tone in BPH there has been no report or suggestion that $\alpha_1$-adrenoreceptor antagonists, or their pharmaceutically acceptable acid addition salts could be used to prevent the formation of, or reduce BPH in a mammal.

SUMMARY OF THE INVENTION

It has now been found that drugs consisting of $\alpha_1$-adrenoreceptor antagonists or their pharmaceutically acceptable acid addition salts, when administered to a mammal prior to the onset of BPH can prevent its formation or, after the onset of BPH, can reduce the condition. More specifically, the drugs, when administered in therapeutically effective doses, prevent formation of BPH or if BPH is already present they increase the rate of destruction (apoptosis) of the abnormal cells but do not affect normal cells. Preferably the $\alpha_1$-adrenoreceptor antagonists are selected from the group comprising alfuzosin, indoramin, terazosin, bunazosin, doxazosin and its 6'- and 7'-hydroxy metabolites, prazosin, tamsulosin, abanoquil, Recordati 15/2739 (trademark), RS 17053 (trademark), SL 89.0591 (trademark), other $\alpha_1$-adrenoreceptor antagonists mentioned by Kenny et al. (Id. at pages 917 and 919–20) and the like.

DETAILED DESCRIPTION OF THE INVENTION

This invention relates to the use of drugs comprising $\alpha_1$-adrenoreceptor antagonists and their pharmaceutically acceptable acid addition salts to prevent the formation of BPH or reduce it after formation. $\alpha_1$-Adrenoreceptor antagonists useful in the practice of the invention include alfuzosin, indoramin, terazosin, bunazosin, doxazosin, prazosin, tamsulosin, abanoquil, Recordati 15/2739

(trademark), RS 17053 (trademark), SL 89.0591 (trademark) and the like. Preferably the drugs are selected from prazosin and doxazosin and its 6'- and 7'-hydroxy metabolites, their pharmaceutically acceptable acid addition salts. Most preferred $\alpha_1$-adrenoreceptor antagonists are doxazosin and its 6'- and 7'-hydroxy metabolites.

The preferred pharmaceutically acceptable acid addition salts, of the $\alpha_1$-adrenoreceptor antagonists, for use in the practice of the invention are those prepared from mineral acids such as hydrochloric, sulfuric, nitric and phosphoric; organic acids such as sulfonic acids, e.g. benzenesulfonic (besylic), p-toluenesulfonic (PtSA, tosylic), methanesulfonic (MSA, mesylic) and trifluoromethanesulfonic (triflic); carboxylic acids e.g., acetic, proprionic, benzoic, citric, tartaric, maleic, fumaric, succinic and malic. In the case of polybasic acids such as sulfuric and phosphoric the salts may be formed from any of the ionic forms thereof, e.g., in the case of phosphoric acid from its mono- di- and tribasic forms. A most preferred acid is hydrochloric.

In the prevention of the formation of BPH or reduction thereof after formation the $\alpha_1$-adrenoreceptor antagonists, or their pharmaceutically acceptable acid addition salts (herefter the active compounds) can be administered via oral or parenteral, including transdermal, routes. However, it is generally preferred to administer the active compounds orally. Usually, the active compounds are most desirably admisterd in doses ranging from about 0.01 to about 2.0 mg/kg per day. However, variations will generally be necessary depending upon the weight of the patient. The proper dose for treating or preventing the formation of benign prostatic hyperplasia (BPH) in a specific patient will easily be determined by one who is skilled in the art of prescriibing and/or administering such compounds. In the case of doxazosin, for instance, the effective dosages, for treating hypertension, are from about 0.02 to about 0.60 mg/kg body weight per day with the preferred maximal oral range in man being about 0.15 to about 0.30 mg/kg body weight per day. It is to be understood that other variations may arise which depend upon the species of the patient and its individual response to a particular active compound and formulation for the time period and interval of administering the composition. It is sometimes found that dosages below the aforesaid lower levels are adequate and at other times larger dosages may be required, and administered without undesirable side effects. In the latter case it may be necessary to divide the total dose into smaller doses which can be administered throughout the day or the drug may be be administered in a controlled release formulation.

For purposes of oral administration, tablets containing excipients such as sodium citrate, calcium carbonate and dicalcium phosphate may be employed along with various disintegrants such as a starch, preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed in soft elastic and hard-filled gelatin capsules. When aqueous suspensions and/or elixirs are desired for oral administration, the active compounds may be combined with various sweetening or flavoring agents, coloring matter and, if so desired, emulsifying and/or suspending agents, together with diluents such as water, ethanol, propylene glycol, glycerin and combinations thereof.

Although the preferred mode of administration of the active compounds is oral they may be administered parenterally as well.

For purposes of parenteral administration, solutions of the active compounds in sesame or peanut oil or in aqueous propylene glycol may be employed, as well as sterile aqueous solutions of the corresponding water soluble acid addition salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass, a distomaceous-earth or an unglazed porcelain filter. Preferred filters of this type include the Berkefeld (trademark), the Chamberland (trademark) and the Asbestos Disk-Metal Seitz (trademark) filter, wherein the fluid is sucked into a sterile container with the aid of a suction pump. Needless to say, the necessary steps should be taken throughout the preparation of these injectable solutions to insure that the final products are obtained in a sterile condition.

The active compounds can also be administered transdermally. For purposes of transdermal administration the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancers and inert carriers such as gel-producing materials, mineral oil, emulsifying agents, benzyl alcohol and the like. Specific transdermal flux enhancing compositions are disclosed in pending U.S. patent application Ser. No. 925,641 which is assigned to the assignee of this invention, the teachings of which are incorporated herein, by reference.

The effect of the drugs on apoptosis of the epithelial cells, i.e., those not involved in the portion of prostatic dysfunction, e.g., prostatic outflow obstruction, which are mediated by the sympathetic nervous system was determined by means of the mouse prostatic reconstitution (MPR) system. (See Slawin et al, *Cancer Research*, 53, 4461–5 (1993)).

To determine if TFG-β1 overexpression is involved in BPH pathogenesis we developed a model using the MPR system. Recombinant retroviruses carrying mouse TGF-β1 cDNSs (Babe TGF-β1Gal and Babe TGF-β1Neo) or a control virus (BAG-a) were used to infect urogenital sinus (UGS) cells dissociated from 17-day old C57βL/6 mouse embryos. The UGS cells were then implanted under the renal capsules of adult male mice, where they develop into prostatic tissues under normal conditions. Relative to BAG-a controls, Babe TGF-β1 infected MPRs contained increased numbers of focal lesions composed of benign epithelial hyperplasia as well as stromal cell hyperplasia. Immunostaining of these lesions with K-14 and tGF-β1 antisera revealed predominantly basal epithelial cells surrounded by hyperplastic stroma with TGF-β1 accumulation. In addition, significantly increased numbers of neuronal cells, mostly catecholaminergic, were also associated with Babe TGF-β1 infected MPRs.

Using this model, the effects of doxazosin, an $\alpha_1$-adrenoceptor blocker, on formation of BPH lesions was evaluated. The data in Table I show that administration of doxazosin i.p. (3 mg/kg b.w.) caused a signficant reduction in the wet weight of MPRs infected with Babe TGF-$\beta$1 (39.2±4.8 mg, mean±S.E.), when compared to controls (55.6±5.52 mg, p<0.05) injected with sterile water only.

TABLE I

| 1<br>Column 1 | 2<br>Control* | 3<br>Doxazosin* | 4<br>se-c* | 5<br>se-d* |
|---|---|---|---|---|
| Babe TGF-$\beta$1 | 55.63 | 39.2 | 5.519 | 4.807 |

*values = mg; c = control; d = doxazosin

Immunohistochemistry revealed no major difference in PCNA labeling between the doxazosin-treated and untreated groups. In contrast, a significantly increased apoptotic rate (AI) in the epithelia of Babe TGF-$\beta$1 infected MPRs was observed in the doxazosin treated group (AI=4.7) relative to the untreated group (AI=3.1, p<0.05).

TABLE II

| | 1<br>Column 1 | 2<br>Control* | 3<br>Doxazosin* | 4<br>se-c | 5<br>se-d |
|---|---|---|---|---|---|
| 1 | BabetGF-$\beta$1 | 3.143 | 4.743 | 0.812 | 0.394 |

*Values indicate apoptotic bodies/1000 epihtelial cells. See Table I for other definitions.

Values indicate apoptotic bodies/1000 epihtelial cells. See Table I for other definitions.

Thus, it was seen that doxazosin had a pronounced effect on the formation, or destruction, of BPH. It did not have any effect on the apoptosis of normal cells. The mechanism of action for doxazosin in preventing the formation of, or destroying, BPH appears to involve induction of apoptosis within the context of prostatic development. However, the invention does not depend upon the accuracy of any theory with respect to the its mechanism.

What is claimed is:

1. A method for reducing the extent of or preventing further hyperplasia BPH in a mammal which comprises administering to said mammal an amount of a drug comprising an $\alpha_1$-adrenoreceptor antagonist, or pharmaceutically acceptable acid addition salt thereof, effective for reducing the extent of or preventing the BPH, wherein the $\alpha_1$-adrenoreceptor antagonist is selected from prazosin, doxazosin and its 6'- and 7'-hydroxy metabolites and pharmaceutically acceptable acid addition salts thereof.

2. The method according to claim 1 wherein the $\alpha_1$-adrenoreceptor antagonist is doxazosin and its 6'- and 7'-hydroxy metabolites.

3. The method according to claim 2 wherein the $\alpha_1$-adrenoreceptor antagonist is the 6'-hydroxy metabolite of doxazosin.

4. The method according to claim 2 wherein the $\alpha_1$-adrenoreceptor antagonist is the 7'-hydroxy metabolite of doxazosin.

5. The method according to claim 2 wherein said drug is administered orally.

6. The method according to claim 2 wherein said drug is administered intraperitoneally.

7. The method according to claim 2 wherein said drug is administered transdermally.

8. The method according to claim 2 wherein said drug is administered parenterally.

9. The method according to claim 2 wherein the daily dose of said drug is divided into smaller portions to be administered several times during the day.

10. The method according to claim 2 wherein the daily dose of said drug is administered in a controlled release formulation.

* * * * *